US009566131B2

(12) United States Patent
Lee et al.

(10) Patent No.: US 9,566,131 B2
(45) Date of Patent: Feb. 14, 2017

(54) ENDODONTIC FILE WITH HIGH FATIGUE RESISTANCE

(71) Applicant: MING CHI UNIVERSITY OF TECHNOLOGY, New Taipei (TW)

(72) Inventors: Jyh-Wei Lee, New Taipei (TW);
Yu-Lun Deng, New Taipei (TW);
Chun-Pin Lin, New Taipei (TW)

(73) Assignee: MING CHI UNIVERSITY OF TECHNOLOGY, New Taipei (TW)

( * ) Notice: Subject to any disclaimer, the term of this patent is extended or adjusted under 35 U.S.C. 154(b) by 13 days.

(21) Appl. No.: 14/711,136

(22) Filed: May 13, 2015

(65) Prior Publication Data

US 2016/0256237 A1 Sep. 8, 2016

(30) Foreign Application Priority Data

Mar. 6, 2015 (TW) ............................... 104107138 A

(51) Int. Cl.
*A61C 5/02* (2006.01)
(52) U.S. Cl.
CPC ......... *A61C 5/023* (2013.01); *A61C 2201/007* (2013.01)
(58) Field of Classification Search
CPC ......... A61C 5/023; A61C 1/082; A61C 19/02; A61C 5/028; A61C 5/025; A61K 6/00; A61K 21/00
See application file for complete search history.

(56) References Cited

U.S. PATENT DOCUMENTS

| 5,399,435 A * | 3/1995 | Ando | B32B 17/10174 428/428 |
| 6,503,599 B1 * | 1/2003 | Tojo | C08J 5/18 428/212 |
| 6,797,335 B1 * | 9/2004 | Paderov | C23C 14/22 427/528 |
| 7,939,172 B2 * | 5/2011 | Gorokhovsky | C22C 38/44 428/216 |
| 2007/0284255 A1 * | 12/2007 | Gorokhovsky | C22C 38/44 205/89 |
| 2009/0113726 A1 * | 5/2009 | Ducros | B26B 21/60 30/346.53 |
| 2011/0033822 A1 * | 2/2011 | Bahcall | A61C 5/023 433/102 |
| 2013/0177871 A1 * | 7/2013 | Tenne | A61C 5/023 433/102 |
| 2015/0284840 A1 * | 10/2015 | Henn | C23C 14/34 428/201 |

OTHER PUBLICATIONS

Monteverde et al., Processing and properties of zirconium diboride based composites, Mar. 28, 2001, Elsevier,22, 279-288.*
Tavadze and Shteinberg, Production of Advanced Materials by Methods of Self-Propagating High-Temperature Synthesis, 2013, SpringBrief in Materials, 43-81.*
Jayaraj et al., Corrosion Behaviour of Ni—Zr—Ti—Si—Sn amorphous plasma spray coating, Aug. 25, 2005, Elsevier, 48,950-964.*

* cited by examiner

*Primary Examiner* — Cris L Rodriguez
*Assistant Examiner* — Shannel Wright
(74) *Attorney, Agent, or Firm* — Muncy, Geissler, Olds & Lowe, P.C.

(57) ABSTRACT

An endodontic file with improved fatigue resistance comprising a conical body made of a metal alloy and an amorphous titanium-zirconium-boron film deposited on a surface of the conical body.

8 Claims, 8 Drawing Sheets

ENDODONTIC FILE WITH HIGH FATIGUE RESISTANCE

CROSS REFERENCE

The non-provisional application claims priority from Taiwan Patent Application NO. 104107138, filed on Mar. 6, 2015, the content thereof is incorporated by reference herein.

FIELD OF THE INVENTION

The present invention relates to an improved endodontic file, and particularly to an endodontic file with high fatigue resistance.

BACKGROUND OF THE INVENTION

During endodontic treatment, an endodontic file is used for the debridement of an infected pulp tissue. The endodontic file is mostly made of a metal alloy, e.g. a nickel-titanium (Ni—Ti) alloy, but usually exhibits fatigue problems. For this reason, when the endodontic file is placed in the root canal of a patient in need of the treatment, the file is likely to be fractured when rotated in the root canal for a long period. Upon fracture, a dentist must stop the treatment at once and try to remove the fraction from the root canal. This not only extends the treatment period, but also possibly hurts the patient when the fraction can't be easily removed.

Therefore, there is a need to solve the fatigue problem exhibited in the conventional endodontic file.

SUMMARY OF THE INVENTION

An objective of the invention is to provide a novel endodontic file, which is highly fatigue-resistant and thus can overcome the fatigue problem of the conventional endodontic file.

For the and/or other objective(s), the present invention discloses an endodontic file comprising: a conical body and an amorphous titanium-zirconium-boron (Ti—Zr—B) film. The conical body is made of a metal alloy, and the film is positioned on a surface of the conical body.

When forces are applied to the endodontic file for multiple times, the applied forces can't act on the same point of the file. Accordingly, fatigue resulting from the applied forces on the file can be reduced, and probability of fracturing the file can also be reduced.

DETAILED DESCRIPTION OF THE INVENTION

Figure 1:
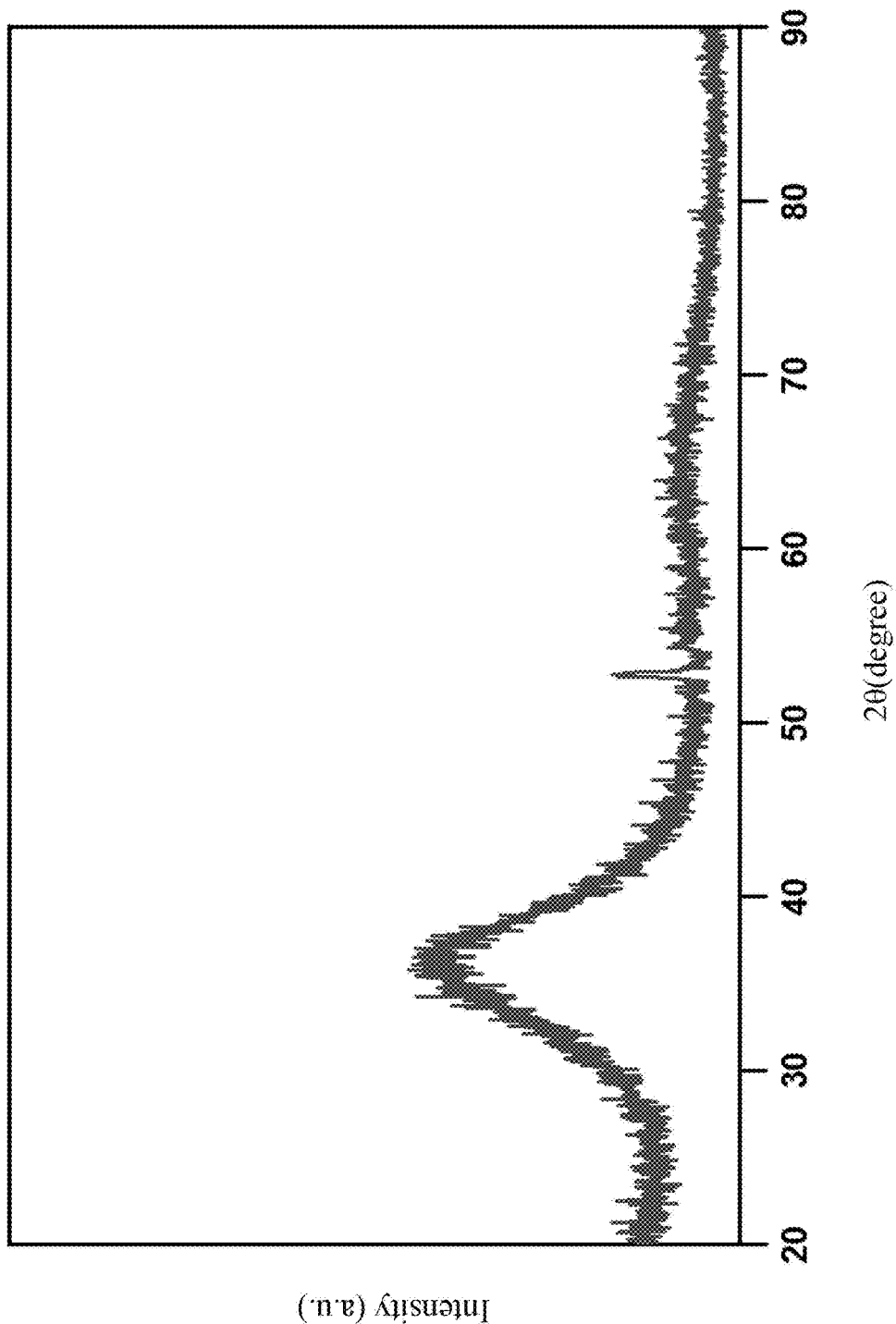
FIG. 1 is an X-ray diffraction diagram illustrating the crystal structure of the film in Example 1.

The detailed description and preferred embodiments of the invention will be set forth in the following content, and provided for people skilled in the art so as to understand the characteristics of the invention.

In an embodiment of the present invention, an endodontic file is disclosed, which improves the fatigue problem of the prior endodontic file. The endodontic file in the embodiment comprises: a conical body and an amorphous titanium-zirconium-boron film.

The conical body comprises a metal alloy, and an example of the metal alloy is, but not limited to, a nickel-titanium alloy. The amorphous film is positioned on a surface of the conical body. Note that a crystalline titanium-zirconium-boron film is not used in the embodiment for the following reasons:

1. The amorphous film has an amorphous structure so that the forces applied to the file for multiple times can act on different points thereof. Therefore, the fatigue caused by the forces on the file can be reduced.

2. Conversely, if the crystalline film is substituted for the amorphous film in the file, the crystalline film can let the multiple times' forces act on the same point of the file so as to increase the fatigue on the file.

Theoretically, there is no limitation to the thickness of the amorphous film, as long as the foregoing effect can be reached. The thickness is preferably 200-500 nm. Theoretically, there is no limitation to the method for forming the amorphous film on the conical body, as long as the foregoing effect can be reached. The method is preferably physical vapor deposition (PVD), and more preferably evaporation deposition or sputtering deposition.

The following examples are offered to further illustrate the invention.

EXAMPLE 1

A magnetron sputter was used to deposit an amorphous titanium-zirconium-boron film with a 200 nm thickness on the surface of a commercial endodontic file made of a pure nickel-titanium alloy to manufacture an endodontic file, or on the surface of a 420 stainless steel block. In the deposition, pulsed direct current powers were supplied to a titanium target (5×12 inch) and to a boron target (5×12 inch), a radio frequency power was supplied to a zirconium target, and a substrate bias was supplied to the commercial endodontic file or the 420 stainless steel block. Furthermore, the commercial endodontic file or the 420 stainless steel block was placed on a holder with an equivalent distance to each target in the deposition. The deposition conditions are listed in Table 1 below.

TABLE 1

Conditions for depositing the film in Example 1

| | | |
|---|---|---|
| | base pressure (Pa) | $4 \times 10^{-3}$ |
| | working pressure (Pa) | $4 \times 10^{-1}$ |
| | deposition time (hr) | 1.5 |
| | deposition gas: argon (sccm) | 40 |
| target parameters | titanium target (power of the pulsed direct current power, W) | 500 |
| | zirconium target (power of the radio frequency power, W) | 500 |
| | boron target (power of the pulsed direct current power, W) | 450 |
| | frequency of the pulsed direct current power (kHz) | 20 |
| | reverse time of the pulsed direct current power (µs) | 5 |
| | substrate bias (V) | −100 |
| | rotation speed of the holder (rpm) | 20 |

EXAMPLE 2

In the instant example, an amorphous titanium-zirconium-boron film with a 500 nm thickness was deposited on the surface of a commercial endodontic file made of a pure nickel-titanium alloy to produce an endodontic file, or on the surface of a 420 stainless steel block. The deposition was implemented as described in Example 1, except that the deposition time was 2.5 hr.

Test 1

Firstly, the composition of the film in Example 1 was analyzed. The result shows the film is composed of 44.3±0.5at. % titanium atoms, 31.1±0.2at % zirconium atoms, 21.1±0.5at % boron atoms, and 3.6±0.3at % oxygen atoms.

Secondly, an X-ray diffractometer was used to analyze the crystal structure of the film in Example 1. As shown in FIG. 1, there is a broad peak to indicate that the crystal structure is amorphous.

Thirdly, an atomic force microscope (AFM) was introduced to calculate the surface roughness of the film in Example 1. The result shows that the average roughness (Ra) is 0.3±0.1 nm, the maximum height (Rmax) is 3.5±0.5 nm, and the root-mean-square roughness (Rms) is 0.3±0.1 nm.

Figure 2B:
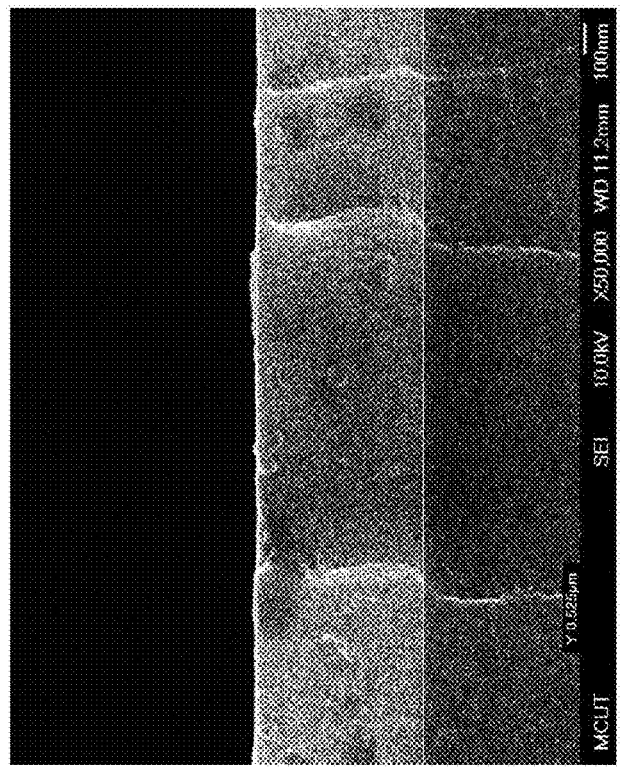
FIG. 2B is a scanning electron microscope picture showing the cross section of the film in Example 1.
Figure 2A:
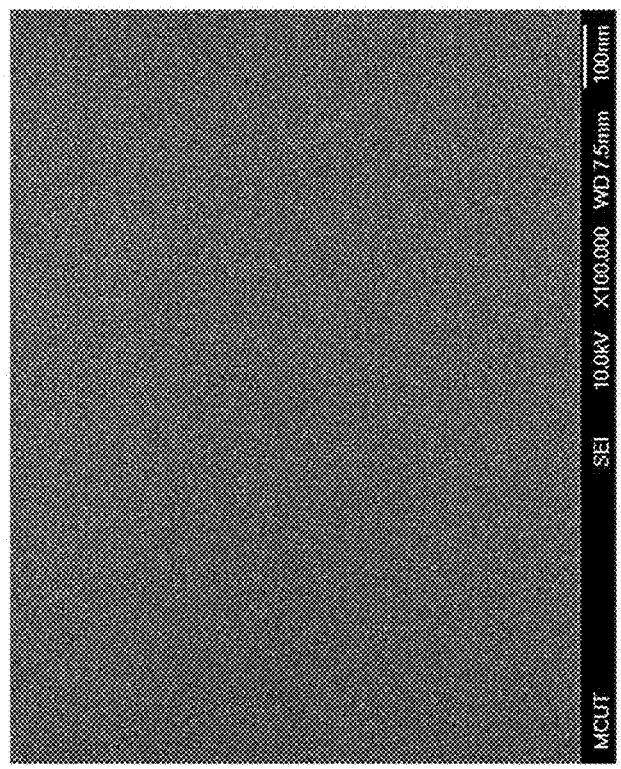
FIG. 2A is a scanning electron microscope (SEM) picture showing the surface of the film in Example 1.
Figure 3:
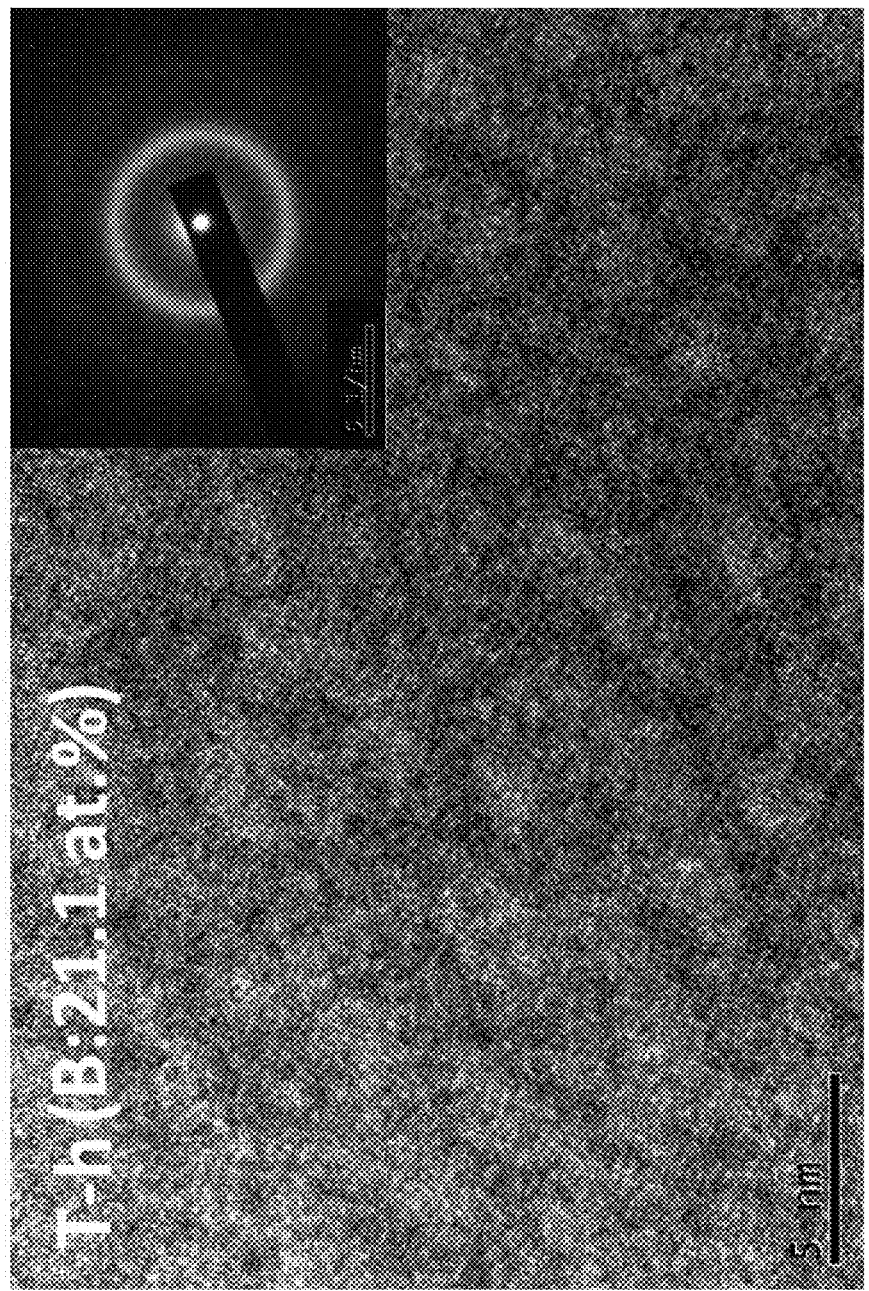
FIG. 3 is a transmission electron microscope (TEM) picture showing the film in Example 1.

Finally, a scanning electron microscope and a transmission electron microscope were used to observe the film in Example 1. As shown in FIGS. 2A-B, and 3, the film in Example 1 appears condensed without crystals or nanocrystallites. These figures further show that the thickness of the film in Example 1 is 200 nm. As described above, the film in Example 1 is amorphous.

Test 2

A nano-indentation test was used to analyze the mechanical behavior of the film in Example 1. The result shows that the hardness is 6.2±0.6 GPa, the elastic coefficient is 116±7 GPa, and the hardness/elastic coefficient (H/E) value is 0.046-0.057.

Figure 4:
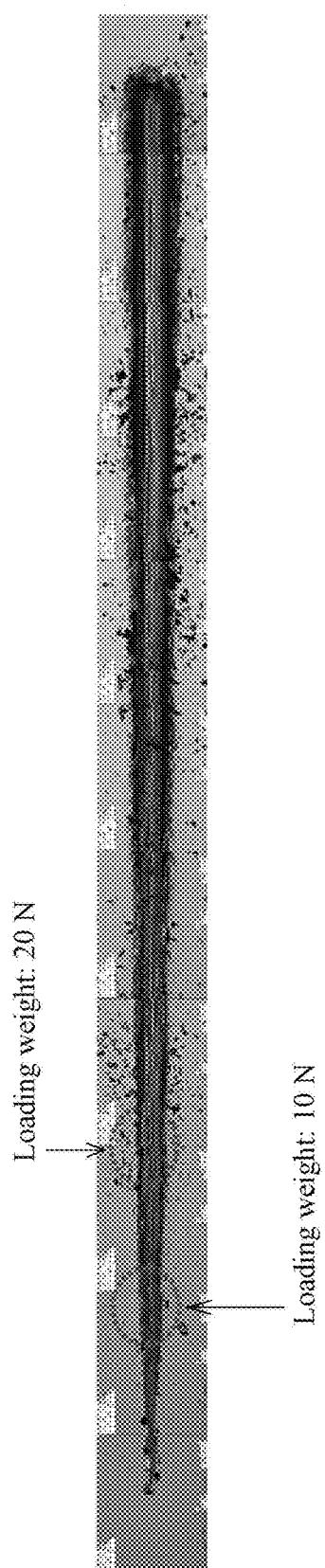
FIG. 4 is a picture showing the adhesion status of the film in Example 1 on a 420 stainless steel block after a scratch test with various loading weights.
Figure 5B:
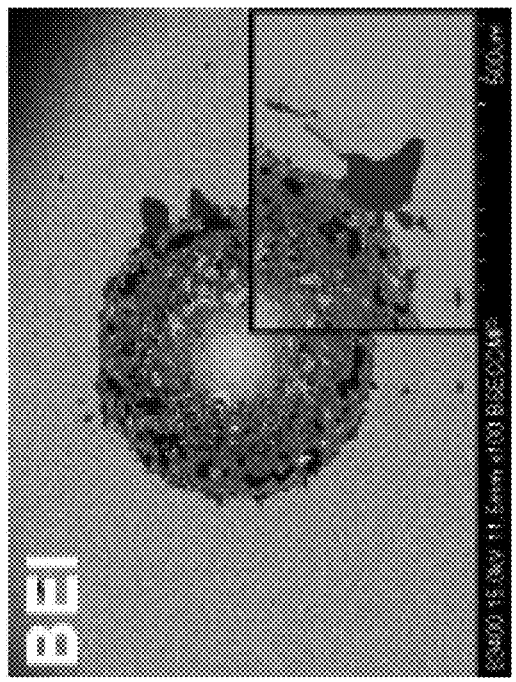
FIG. 5B is a back scattered electron imaging (BEI) microscope picture showing the adhesion status of the film in Example 1 on a 420 stainless steel block after an HRC-DB test.
Figure 5A:
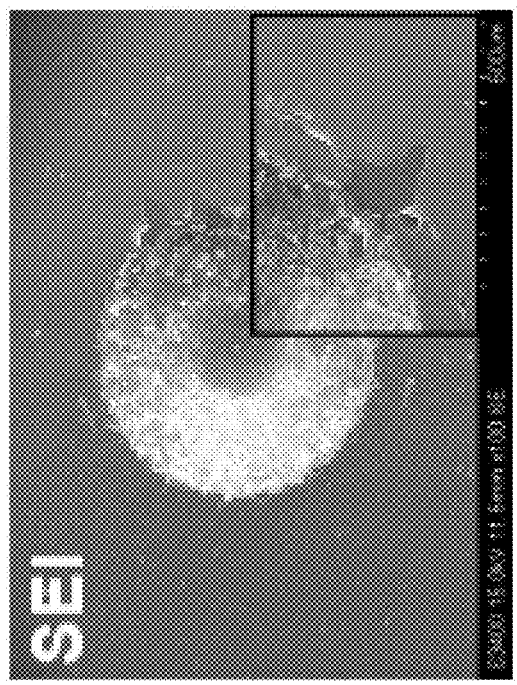
FIG. 5A is a second electron imaging (SEI) microscope picture showing the adhesion status of the film in Example 1 on a 420 stainless steel block after a Daimler-Benz Rockwell-C (HRC-DB) test.

A scratch test with different loading weights and an HRC-DB test were used to analyze the adhesion status of the film in Example 1 on the 420 stainless steel block. As shown in FIGS. 4, and 5A-B, the film in Example 1 still adheres to the 420 stainless steel block after these tests. Also, the HRC-DB result shows that the adhesion degree is HF3.

Test 3

Figure 6:
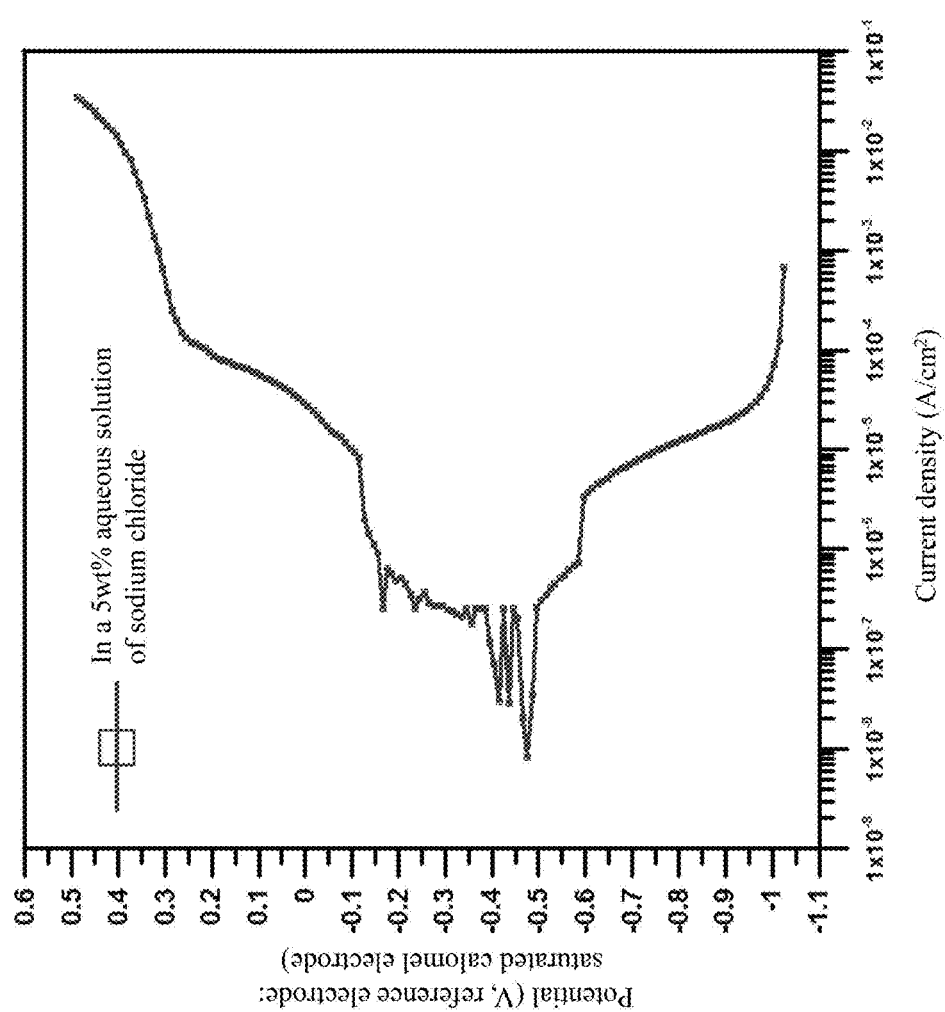
FIG. 6 is a diagram illustrating the corrosion status of the film in Example 1 in a 5wt % aqueous solution of sodium chloride.

The endodontic file in Example 1 was placed in a 5wt % aqueous solution of sodium chloride for a potentiodynamic polarization corrosion test, so that the corrosion characteristics of the file thereof were measured. As shown in FIG. 6, the corrosion potential (Ecorr) is −0.47 V, the corrosion current density (Icon) is 0.04 µA/cm², the pitting potential (Epit) is −0.125 V, and the pitting current density (Ipit) is 1.97 µA/cm².

Test 4

Figure 7:
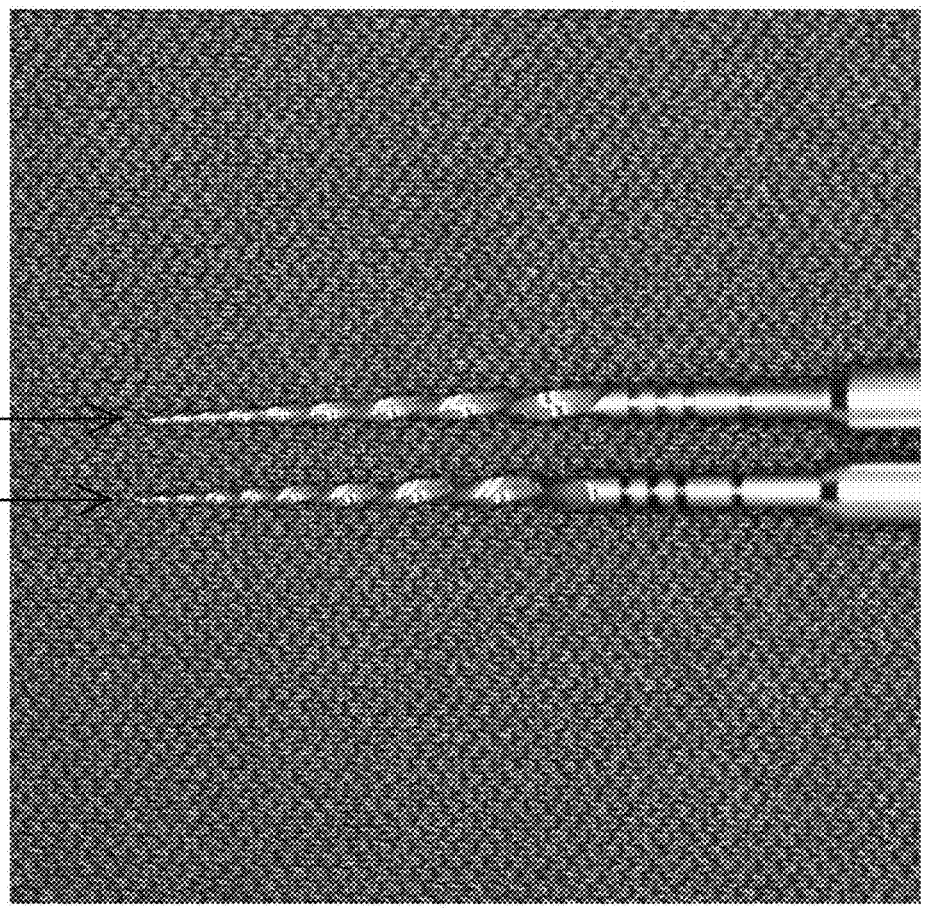
FIG. 7 is a picture comparing the endodontic file in Example 1 with a commercial endodontic file.

As shown in FIG. 7, the endodontic file in Example 1 appears similar with the commercial one. In another unshown figure, the endodontic file in Example 2 also appears similar with the commercial one.

A reciprocating bending fatigue test was used to analyze the fatigue performance of the endodontic file in Example 2 and that of the commercial one. In the test, each file was pressed between two stainless bodies. Each file was rotated back and forth in an angle of 60 degrees by the waveone model, until it was fractured. The test was repeated for five times. Herein, the term "fracture period" means the total rotation period to the fracture, and a unit thereof is second. As listed in Table 2 below, the fracture period of the file in Example 2 is about 1.5 times higher than that of the commercial file. This suggests that the file in Example 2 has a greater fatigue resistance than the commercial file.

TABLE 2

Fracture periods of the endodontic file in Example 2 and the commercial endodontic file

| | test number | | | | | | standard |
|---|---|---|---|---|---|---|---|
| | 1 | 2 | 3 | 4 | 5 | average | deviation |
| Commercial | 241.2 | 325.1 | 346.8 | 240.7 | 273 | 285.4 | 48.61 |
| Example 2 | 480.8 | 451.8 | 360.6 | — | — | 431.1 | 62.72 |

Figure 8:
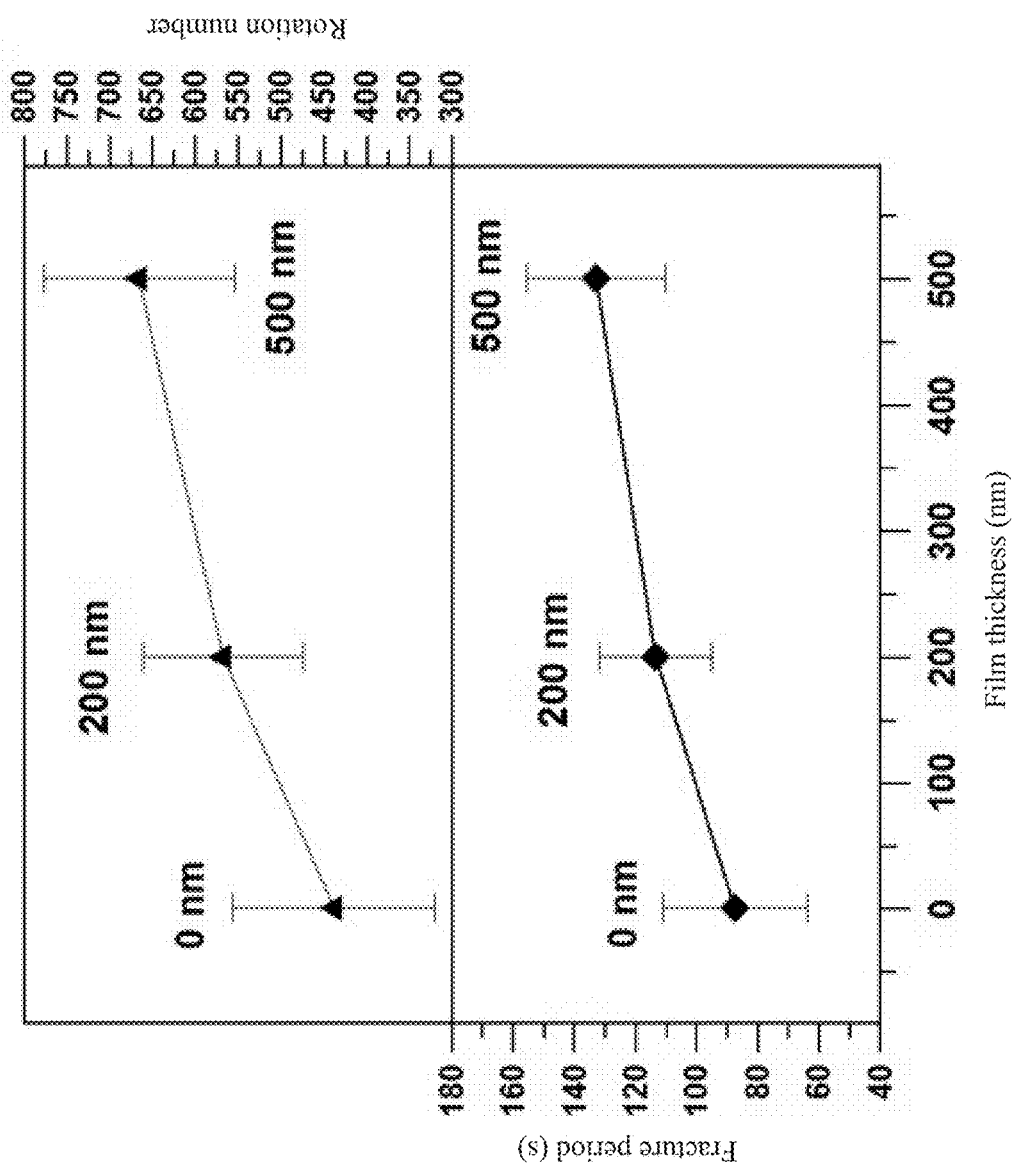
FIG. 8 is a diagram comparing the fatigue resistance of the endodontic files in Examples 1-2 with that of the commercial endodontic file.

A continuous rotation fatigue test was used to analyze the fatigue performance of the files in Examples 1-2 and the commercial one. In the test, each file was pressed between two stainless bodies. Each file was continuously rotated, until it was fractured. The test was repeated for 5-7 times. Herein, the definition and unit of the term "fracture period" comply with those previously described, and the term "rotation number" means the number of rotation cycles to the fracture. As listed in Table 3 below, the fracture period of the file in Example 1 is about 1.3 times higher than that of the commercial file, and the fracture period of the file in Example 2 is about 1.5 times higher than that of the commercial file. As listed in Table 4 below, the rotation number of the file in Example 1 is about 1.3 times higher than that of the commercial file, and the rotation number of the file in Example 2 is about 1.5 times higher than that of the commercial file. The above differences are especially presented in FIG. 8. As described above, the endodontic files in Examples 1-2 are proven to be more fatigue resistant than the commercial endodontic file.

TABLE 3

Fracture periods of the endodontic files in Examples 1-2 and the commercial endodontic file

| | test number | | | | | | | average | standard deviation |
|---|---|---|---|---|---|---|---|---|---|
| | 1 | 2 | 3 | 4 | 5 | 6 | 7 | | |
| Commercial | 66.1 | 65.2 | 105.8 | 83.1 | 117.8 | — | — | 87.6 | 23.6 |
| Example 1 | 96.8 | 110.8 | 151.7 | 98 | 109 | 119.4 | 109.5 | 113.6 | 18.5 |
| Example 2 | 132.4 | 117.3 | 105.4 | 152.6 | 158 | — | — | 133.1 | 22.5 |

TABLE 4

Rotation numbers of the endodontic files in Examples 1-2 and the commercial endodontic file

| | test number | | | | | | | average | standard deviation |
|---|---|---|---|---|---|---|---|---|---|
| | 1 | 2 | 3 | 4 | 5 | 6 | 7 | | |
| Commercial | 330.5 | 326 | 529 | 415.5 | 589 | — | — | 438 | 117.983 |
| Example 1 | 484 | 554 | 758.5 | 490 | 545 | 597 | 547.5 | 568 | 92.56667 |
| Example 2 | 662 | 586.5 | 527 | 763 | 790 | — | — | 665.7 | 112.3 |

In conclusion, the endodontic file in the embodiment has high fatigue resistance. As a result, probability of fracturing the endodontic file can be reduced after force application thereto for multiple times. That is, the endodontic file in the embodiment is more suitable for use in endodontic treatment than any prior endodontic file.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An endodontic file, consisting of:
   a conical body made of a metal alloy; and
   an amorphous titanium-zirconium-boron film deposited on a surface of the conical body.

2. The endodontic file as claimed in claim 1, wherein the metal alloy is a nickel-titanium alloy.

3. The endodontic file as claimed in claim 2, wherein a thickness of the film is 200 nm.

4. The endodontic file as claimed in claim 1, wherein the film is formed on the surface of the conical body through physical vapor deposition.

5. The endodontic file as claimed in claim 4, wherein the physical vapor deposition is evaporation deposition or sputtering deposition.

6. The endodontic file as claimed in claim 3, wherein the film has a hardness of 6.2±0.6 GPa, an elastic coefficient of 116±7 GPa, and a hardness/elastic coefficient (H/E) value of 0.046-0.057.

7. The endodontic file as claimed in claim 3, wherein the film has a corrosion potential of −0.47 V, and a corrosion current density of 0.04 μA/cm2.

8. The endodontic file as claimed in claim 3, wherein the film has an average roughness of 0.3±0.1 nm, a maximum height of 3.5±0.5 nm, and a root-mean-square roughness of 0.3±0.1 nm.

* * * * *